US007002692B2

(12) United States Patent
Akao et al.

(10) Patent No.: US 7,002,692 B2
(45) Date of Patent: Feb. 21, 2006

(54) INFRARED CIRCULAR DICHROISM MEASURING APPARATUS AND INFRARED CIRCULAR DICHROISM MEASURING METHOD

(75) Inventors: Kenichi Akao, Hachioji (JP); Jun Koshoubu, Hachioji (JP)

(73) Assignee: Jasco Corporation, Tokyo (JP)

( * ) Notice: Subject to any disclaimer, the term of this patent is extended or adjusted under 35 U.S.C. 154(b) by 310 days.

(21) Appl. No.: 10/457,400

(22) Filed: Jun. 10, 2003

(65) Prior Publication Data

US 2003/0234937 A1    Dec. 25, 2003

(30) Foreign Application Priority Data

Jun. 20, 2002    (JP)    ............................. 2002-180249

(51) Int. Cl.
*G01B 9/02*    (2006.01)
(52) U.S. Cl. ..................................................... 356/491
(58) Field of Classification Search ................ 356/451, 356/452, 491
See application file for complete search history.

(56) References Cited

U.S. PATENT DOCUMENTS 5,708,504 A * 1/1998 Hopkins ..................... 356/456
5,788,632 A   8/1998 Pezzaniti et al.
6,070,093 A   5/2000 Oosta et al.

FOREIGN PATENT DOCUMENTS

| EP | 0 916 945 A1 | 5/1999 |
| JP | A 2000-206036 | 7/2000 |
| WO | WO 01/63231 A1 | 8/2001 |

* cited by examiner

*Primary Examiner*—Zandra V. Smith
*Assistant Examiner*—Michael A. Lyons
(74) *Attorney, Agent, or Firm*—Oliff & Berridge, PLC

(57) ABSTRACT

The object of the invention is to provide an infrared circular dichroism measuring apparatus that improves the measuring time and the measuring accuracy.

An infrared circular dichroism measuring apparatus 101 comprising: AC signal extractors 110–112 where an interference light beam from an IR light source 102 which has passed an interferometer 103 is converted into a clockwise and a counterclockwise circularly polarized light beams and is irradiated on a sample to extract from a detected signal of detector 107 an interferogram by each of the circularly polarized light beams; DC signal extractors 113, 112 for extracting an interferogram by the IR absorption of the sample; a calculator 114 for figuring out the circular dichroism; and a selective transmitter 120 for narrowing down the wavelength region to be measured based on an IR absorption wavelength region corresponding to a vibration mode of the structure to be measured in the sample molecule.

13 Claims, 7 Drawing Sheets

INFRARED CIRCULAR DICHROISM MEASURING APPARATUS AND INFRARED CIRCULAR DICHROISM MEASURING METHOD

RELATED APPLICATIONS

This application claims priority to the Japanese Patent Application 2002-180249 dated on June 20, 2002 and is hereby incorporated with reference for all purposes.

BACKGROUND OF THE INVENTION

1. Field of the Invention

The present invention relates generally to an infrared circular dichroism measuring apparatus and an infrared circular dichroism measuring method, and more particularly to a reduction of the measuring time and an improvement of the measuring accuracy.

2. Prior Art

For many chemical substances, findings relating to their absolute structures and stereo-structures are extremely basic and essential information. X-ray structural analysis, circular dichroism spectrum analysis, etc. can be referred to as means for analyzing the chirality of physiologically active substances such as, for example, drugs, poisons and biological substances. The circular dichroism spectrum analysis is especially widely used as important and essential means for the studies in this field since it is relatively easy to handle.

Molecules having mirror-image-asymmetric molecular structures have a property that the magnitudes of their absorption for clockwise-circular-polarized light beams and counterclockwise-circular-polarized light beams are different. This property is called circular dichroism. Many physiologically active substances have the optical activity and information about their molecular stereo-structures can be obtained by measuring their circular dichroism. The information obtained in this way is used in identifying their structures.

Infrared circular dichroism measurement can be used especially in identifying the structures of optical active substances that do not have absorption in, for example, UV and visible light regions.

FIG. 5 is a schematic representation of a conventional infrared circular dichroism measuring apparatus. In the infrared circular dichroism measuring apparatus 1 shown in the figure, an interference light beam is generated by passing an infrared light beam radiated from an IR light source 2 through a Michelson interferometer 3. On the optical path of the interference light beam, a polarizer 4, a photoelastic modulator (PEM) 5, a sample 6 and a detector 7 are provided. The interference light beam becomes a linearly polarized light beam by being passed through the polarizer 4 and the linearly polarized light beam is converted by PEM 5 into a circularly polarized light beam that is generated in clockwise and counterclockwise alternately at a predetermined modulation frequency. The modulation frequency of PEM 5 is controlled by a PEM controller 8. The infrared light beam modulated in this way is detected by the detector 7 after passing the sample 6. A detector that can respond quickly to be able to cope with the PEM frequency around 50 KHz such as PC-type MCT detector is used as the detector 7.

At this moment, a signal shown in FIG. 6 is detected by the detector 7. That is, for example, when a clockwise and counterclockwise circular polarized light beam is generated at a modulation frequency of 50 KHz by the PEM controller, the signal detected after its passing through the sample must have an alternate-current component modulated at the modulation frequency of PEM 5 because the sample that is an optical active substance has different magnitudes of its absorption for a clockwise circular polarized light beam and a counterclockwise circular polarized light beam. Then, a doubly modulated signal in which the alternate-current component is superposed on the modulation (at lower 3 KHz) by the interferometer 3 is detected.

Interferograms produced by each of the clockwise and counterclockwise circularly polarized light beams are extracted from the signal detected at the detector 7 by, after being amplified at a pre amplifier 9, passing through a band pass filter 10, a lock in amplifier 11 and a data acquisition circuit 12. That is, the band-pass filter 10 passes therethrough only a signal in a predetermined frequency band containing the modulation frequency of PEM 5 and the lock in amplifier 11 lock-in-detects the component having the modulation frequency of PEM 5 using a synchronized signal. At this moment, the detected component is sampled with a predetermined time constant (the time period necessary between the moment the lock in amplifier outputs a measured signal and the moment the amplifier outputs the next measured signal) and an alternate current having an intensity variation of the modulated component at lower 3 KHz by the interferometer 3 is obtained.

On the other hand, an interferogram by infrared absorption is extracted by, after amplifying the signal detected at the detector 7, passing the signal through a low pass filter 13 and the data acquisition circuit 12.

Based on the interferograms produced from each of the clockwise and counterclockwise circularly polarized light beams and the interferograms produced from the infrared absorption extracted as above, a Fourier transformation is conducted at a host PC 14 to calculate a circular dichroism spectrum that is the difference spectrum (ΔA) between absorption spectra produced from each of clockwise and counterclockwise polarized light beams.

In an infrared circular dichroism measurement, the intensity of a signal obtained is weak and, therefore, a measurement is conducted by radiating a multi-wavelength infrared light beam to a sample at the same time using a Fourier transform infrared spectrometer. Therefore, this measurement has the following problems.

First, at the central wavelength of the PEM, i.e., a narrow region around the light beam wavelength that has the most high efficiency for generating a circularly polarized light beam, a circularly polarized light beam is efficiently generated, however, in a wavelength region away from that narrow region, the efficiency for generating a circularly polarized light beam is reduced and the measurement efficiency is degraded.

Furthermore, the alternate-current component modulated at the modulation frequency of PEM is very faint (the absorbance A is ordinarily around 1, however, it is around $10^{-4}$–$10^{-5}$ for a circular dichroism measurement) because the difference between the absorption spectra produced from each of clockwise and counterclockwise circularly polarized light beams is very small. Therefore, a plurality of measurement are necessary to improve the S/N ratio and a measurement can not be conducted in a short time (for example, an integration for one (1) to two (2) hours is necessary).

On the other hand, the intensity of the light beam detected is very strong because of light beams each having a wavelength different from each other are contained in the light beam at the same time. Therefore, when a PC-type MCT detector that can respond quickly to be able to cope with the PEM frequency around 50 KHz is used as the detector, a signal in proportion to the light beam intensity can not be output in terms of the regions where the detected light beam intensity is too strong and a non-linear response is occurred, resulting in an adverse influence on the measurement accuracy.

Because the intensity of a modulated signal (interferogram) produced from an interference light beam is rapidly attenuated as shown in FIG. 6, the tail portion where the intensity is weak is influenced strongly by noises. Therefore, the dynamic range in the portion is restrained due to the SIN ratio originated in the influence and quantization error produced during an AD conversion.

In terms of S/N ratio improvement, it is preferable to extend the time constant of the lock in amplifier. However, when sampling of a signal having an intensity variation of the component modulated at lower 3 KHz by the interferometer as shown in FIG. 6 is assumed, it is necessary to measure with a time constant of 1 m·second or shorter and the S/N ratio is limited to a specific extent because the component modulated by the interferometer can not be obtained if the time constant is extended too long.

Furthermore, there is another problem. Since a circular dichroism spectrum is obtained corresponding to the position of an absorption peak, it is possible to know which molecular vibration originates a specific circular dichroism spectrum. However, it is the current state that the relation between information on the molecular structures and the shapes of the circular dichroism spectra have not been made sufficiently clear for infrared circular dichroism. There are up to several absorption peaks in UV and visible light regions, while, in contrast, there are a large number of absorption peaks in the so-called finger-print region of infrared and, therefore, their assignment is very complicated. In above respects, means for clarifying the relation between circular dichroism spectra of specific absorption bands and molecular structures have been sought.

The present invention was conceived in view of the above problems involved in the prior art and its object is to provide an infrared circular dichroism measuring apparatus and an infrared circular dichroism measuring method that achieve improvements in the measuring time and the measuring accuracy.

SUMMARY OF THE INVENTION

In order to attain the above object, an infrared circular dichroism measuring apparatus of the present invention comprises an IR light source, an interferometer, a polarized light beam generator, a circularly polarized light beam generator, a detector, a DC signal extractor, an AC signal extractor, a calculator and a selective transmitter.

Herein, the IR light source radiates IR light beams.

The interferometer allows the IR light beams to interfere to generate an interference light beam.

The polarized light beam generator makes the interference light beam into a linearly polarized light beam.

The circularly polarized light beam generator converts the linearly polarized light beam into clockwise and counter clockwise circularly polarized light beams at a predetermined modulation frequency and irradiates the circularly polarized light beams on a sample.

The detector detects the circularly polarized light beams that have passed through the sample, to generate a detection signal.

The DC signal extractor extracts from the detected signal an interferogram by the IR absorption of the sample.

The AC signal extractor extracts from the detected signal an interferogram by each of the clockwise and counterclockwise circularly polarized light beams.

The calculator conducts a Fourier transformation and calculates the circular dichroism and IR absorption, based on each of the interferograms extracted by the extractors.

The selective transmitter narrows down the wavelength region to be measured, based on an IR absorption wavelength region corresponding to a vibration mode of a structure to be measured in the sample molecule.

In the above apparatus, the circularly polarized light beam generator is preferably a photoelastic modulator.

In the above apparatus, the photoelastic modulator preferably sets its central wavelength based on a measurement wavelength region selected by the selective transmitter.

In the above apparatus, the AC signal extractor preferably comprises a lock in amplifier.

In the above apparatus, a wavelength region in which the detector has a high sensitivity is preferably defined based on a wavelength region to be measured selected by the selective transmitter.

In the above apparatus, the selective transmitter is preferably an optical filter and/or an electric filter.

Herein, the optical filter selectively irradiates on the sample a light beam of a wavelength region in an IR absorption band corresponding to a vibration mode of a specific structure in the sample molecule among IR light beams from the IR light source.

The electric filter selectively transmits a signal component of a specific region defined based on a vibration mode of a structure to be measured among interference signals by light beams at each wavelength, that are the components of a signal modulated by the interferometer.

In the above apparatus, the relation between the structure to be measured and the wavelength region selected by the selective transmitter is preferably expressed by at least one of the following to ⑦:

for the structure NH, the wavelength region to be selected for measurement is 3,700–3,100 $cm^{-1}$;

for the structure CH stretching vibration, the wavelength region to be selected for measurement is 3,000–2,800 $cm^{-1}$;

for the structure C=O, the wavelength region to be selected for measurement is around 1,700 $cm^{-1}$;

for the structure amide I (protein), the wavelength region to be selected for measurement is 1,640 $cm^{-1}$;

for the structure amide II (protein), the wavelength region to be selected for measurement is 1,550 $cm^{-1}$;

for the structure CH bending vibration, the wavelength region to be selected for measurement is 1,500–1,300 $cm^{-1}$; and for the structure C-O-C (sugar), the wavelength region to be selected for measurement is 1,100–900 $cm^{-1}$.

In order to achieve the above object, an infrared circular dichroism measuring method of the present invention comprises the steps of:

generating an interference light beam by allowing IR light beams radiated from an IR light source to interfere by use of an interferometer;

after making the interference light beam into a linearly polarized light beam, converting the linearly polarized light beam into a clockwise and a counterclockwise circularly polarized light beams at a predetermined modulation frequency and irradiating the converted light beams on a sample;

detecting the circularly polarized light beams which have passed through the sample and generating a detection signal;

extracting from the detected signal an interferogram by each of the clockwise and the counterclockwise circularly polarized light beams;

conducting a Fourier transformation and calculating a circular dichroism, based on the interferograms; and narrowing down the wavelength region to be measured, based on an IR absorption wavelength region corresponding to a vibration mode of the structure to be measured of a sample molecule.

In the above method, the circularly polarized light beam is preferably generated by a photoelastic modulator.

In the above method, the central wavelength of the photoelastic modulator is preferably set based on the selected wavelength region to be measured.

In the above method, a lock in amplifier is preferably used for the extracting.

In the above method, a detector is preferably used for detecting the circularly polarized light beams which have passed through the sample and generating a detection signal, and a wavelength region in which the detector has a high sensitivity is preferably defined based on the selected wavelength region to be measured.

In the above method, the wavelength region to be measured is preferably narrowed down by selectively irradiating a light beam in an IR absorption wavelength region corresponding to the vibration mode of a specific structure in a sample molecule among the IR light beams from the IR light source, on a sample, using an optical filter, and/or by selectively transmitting a signal component of a specific region defined based on a vibration mode of the structure to be measured among interference signals by light beams at each wavelength, that are components of a signal modulated by the interferometer, using an electric filter.

BEST MODE FOR CARRYING OUT THE INVENTION

Figure 1:
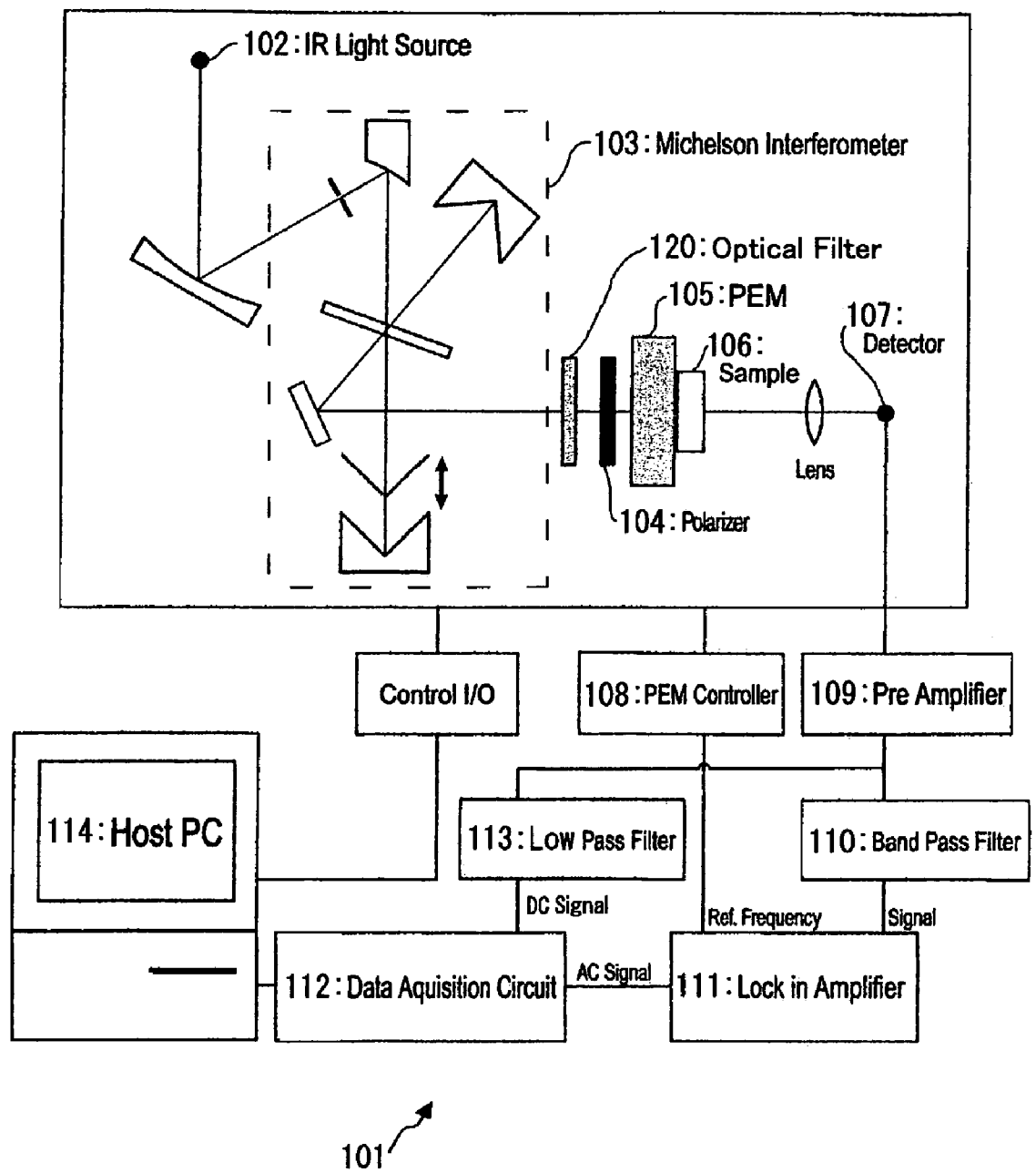
FIG. 1 is a schematic view of an infrared circular dichroism measuring apparatus according to the invention.

The present invention will now be described. The overview of an infrared circular dichroism measuring apparatus according to the invention is shown in FIG. 1. As to components corresponding to those in the above-described conventional art, 100 are added to each of their reference numbers and their descriptions are omitted.

In the infrared circular dichroism measuring apparatus 101 shown in the figure, an interference light beam is generated by passing an infrared light beam radiated from an IR light source 102 through a Michelson interferometer 103 (interferometer).

On the optical path of the interference light beam, an optical filter 120 (selective transmitter), a polarizer 104 (polarized light beam generator), a PEM (photoelastic modulator) 105 (circular polarized light beam generator), a sample 106 and a detector 107 (detector) are provided.

The interference light beam becomes a selectively the specific wavelength region of the light beam by being transmitted through the optical filter 120, and becomes a linearly polarized light beam by being transmitted through the polarizer 104, then, the linearly polarized light beam is converted into a circular polarized light beam that is generated in clockwise and counterclockwise alternately at a predetermined modulation frequency by the PEM 105.

The modulation frequency of PEM 105 is controlled by a PEM controller 108. The infrared light beam modulated in this way is detected by the detector 107 (detector) such as, for example, PC-type MCT detector, PV-type MCT detector or InSb detector, after passing the sample 106.

The present invention is characterized in that a selective transmitter is provided, that transmits selectively only the light in a specific wavelength region in infrared light radiated from an infrared light source, like the optical filter 120.

The wavelength transmitted by this selective transmitter is set based on a wavelength region of an infrared absorption band corresponding to a vibration mode of a specific structure in a sample molecule. That is, the measurement is conducted by selecting the light of a wavelength region necessary for the structural analysis of the sample molecule. The following infrared light absorption bands can be listed as those corresponding to the vibration modes.

| | |
|---|---|
| 3,700–3,100 cm$^{-1}$ | NH |
| 3,000–2,800 cm$^{-1}$ | CH stretching vibration |
| 1,700 cm$^{-1}$ | C=O |
| 1,640 cm$^{-1}$ | amide I (protein) |
| 1,550 cm$^{-1}$ | amide II (protein) |
| 1,500–1,300 cm$^{-1}$ | CH bending vibration |
| 1,100–900 cm$^{-1}$ | C—O—C (sugar) |

The selective transmitter is not especially limited to a specific type if it selectively transmits only the light in a specific wavelength region, such as an interference filter, and the transmitter can be arranged such that it transmits the light in a plurality of separated wavelength regions corresponding to a plurality of vibration modes. The position of the transmitter to be disposed is not especially limited either as long as it is on the optical path.

By providing a selective transmitter and, therefore, narrowing down the wavelength region of the infrared absorption band corresponding to the vibration mode of the specific structure in the sample molecule, means for clarifying easily the relation between circular dichroism spectra of specific absorption bands and the molecular structures even in an infrared region where their assignment is very complicated is obtained.

In addition to the above selective transmitter that transmits selectively the light in optically specific wavelength regions, transmitters that can give the same effects can also be used. That is, a selective transmitter can be arranged by providing an electric filter at a proper position on the path of an electric signal from the detector such that the transmitter passes interference signals of light in specific wavelength regions, that are the components of the signals modulated by the interferometer, selectively among those in each wavelength region.

The electric filter is preferably positioned immediately before an AD converter on the path of the electric signal from the detector. That is, because, considering that noise signals may by picked up even in the middle of the path of the electric signal, signals other than frequency components corresponding to the measured wave number can be most remarkably suppressed at the position immediately before the AD converter.

The electric filter is set such that the filter passes only the signals of frequency components corresponding to the measured wave number regions among the electric signals from the detector. The relation between these measured wave numbers and frequency is described as follows.

f=2v ν where, f is frequency (Hz),

ν is wave number (cm$^{-1}$), v is moving mirror velocity (cm/sec).

Therefore, assuming, for example, the measured wave number region is 3,700–3100 cm$^{-1}$ and the moving mirror velocity of the interferometer is 0.4 cm/sec, the electric filter is set such that the filter passes only the frequency component of 2,960–2,480 Hz in the electric signal from the detector.

Figure 2:
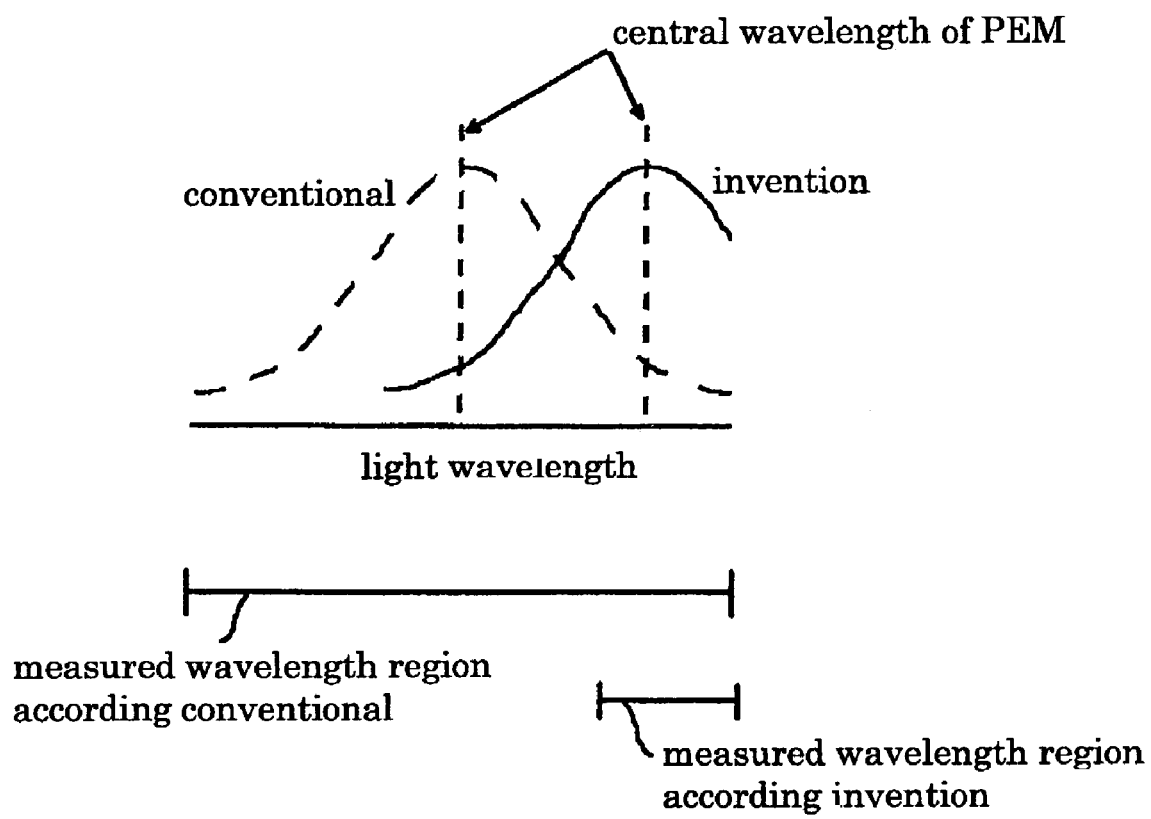
FIG. 2 is a schematic view showing the light-beam-wavelength dependency of the central wave number (the central wavelength) of the PEM.

In this manner, according to the invention, only the light in specific wavelength regions is selectively passed. Therefore, by setting the central wavelength of PEM with the specific wavelength region as shown in FIG. 2, circularly polarized light beams are efficiently generated in all the measured wavelength regions and measurement can be conducted efficiently.

Furthermore, by narrowing down the specific wavelength regions, measurements with high sensitivity can be conducted by utilizing selectively a detector having a high sensitivity in those wavelength regions and, since the integration for improving the S/N ratio can be decreased, the time necessary for the measurement can be shortened.

When a PC-type MCT detector that is preferably used as a detector that responds quickly and can cope with the modulation frequency of PEM, is used, measurement can be conducted without influencing the measurement accuracy since the light in wavelength regions not necessary for the measurement is cut by narrowing down wavelength regions and, therefore, the incident light intensity into the detector is drastically decreased and measurement can be conducted in an intensity range in which linear response can be obtained.

Figure 3:
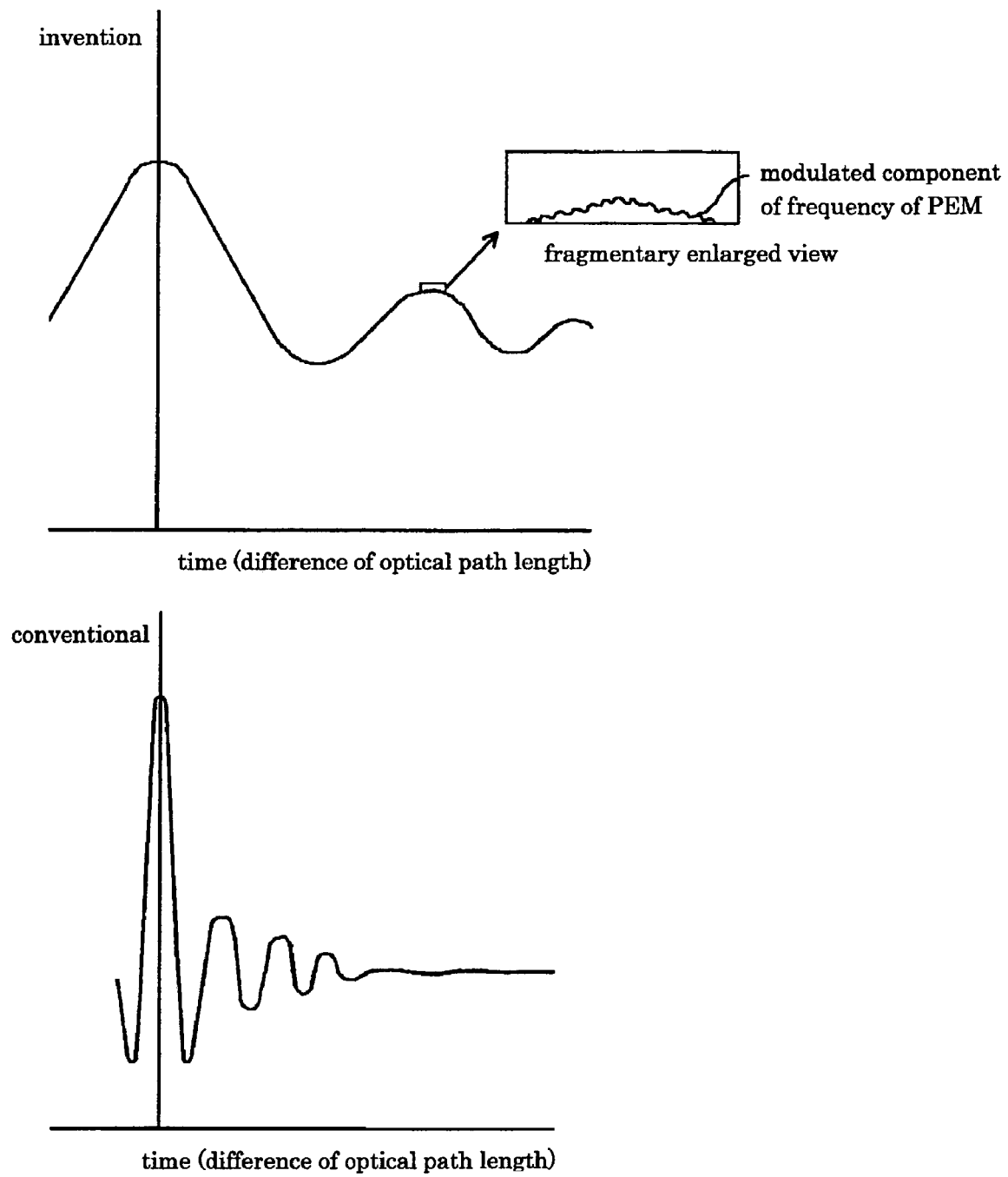
FIG. 3 is an illustrative view of a signal detected by the detector.

A signal of which the overview is shown in FIG. 3 is detected by the detector 107. That is, for example, when clockwise and counterclockwise circular-polarized light beams are generated at a modulation frequency of 50 KHz by the PEM controller, a signal detected after passing through the sample has an alternate current component modulated at the modulation frequency of PEM since the sample which is an optical active substance has different magnitudes of absorption for clockwise circularly polarized light and counterclockwise circularly polarized light. Then, a doubly modulated signal in which this alternate current component is superposed on the modulation by the interferometer 103 is detected.

When an apparatus according to the invention is used, the attenuation of the modulated component by the interferometer in the signal detected by the detector becomes milder compared to the conventional one as shown in FIG. 3 and the frequency of the signal is becomes lower and its shape becomes relatively smoother.

Figure 4:
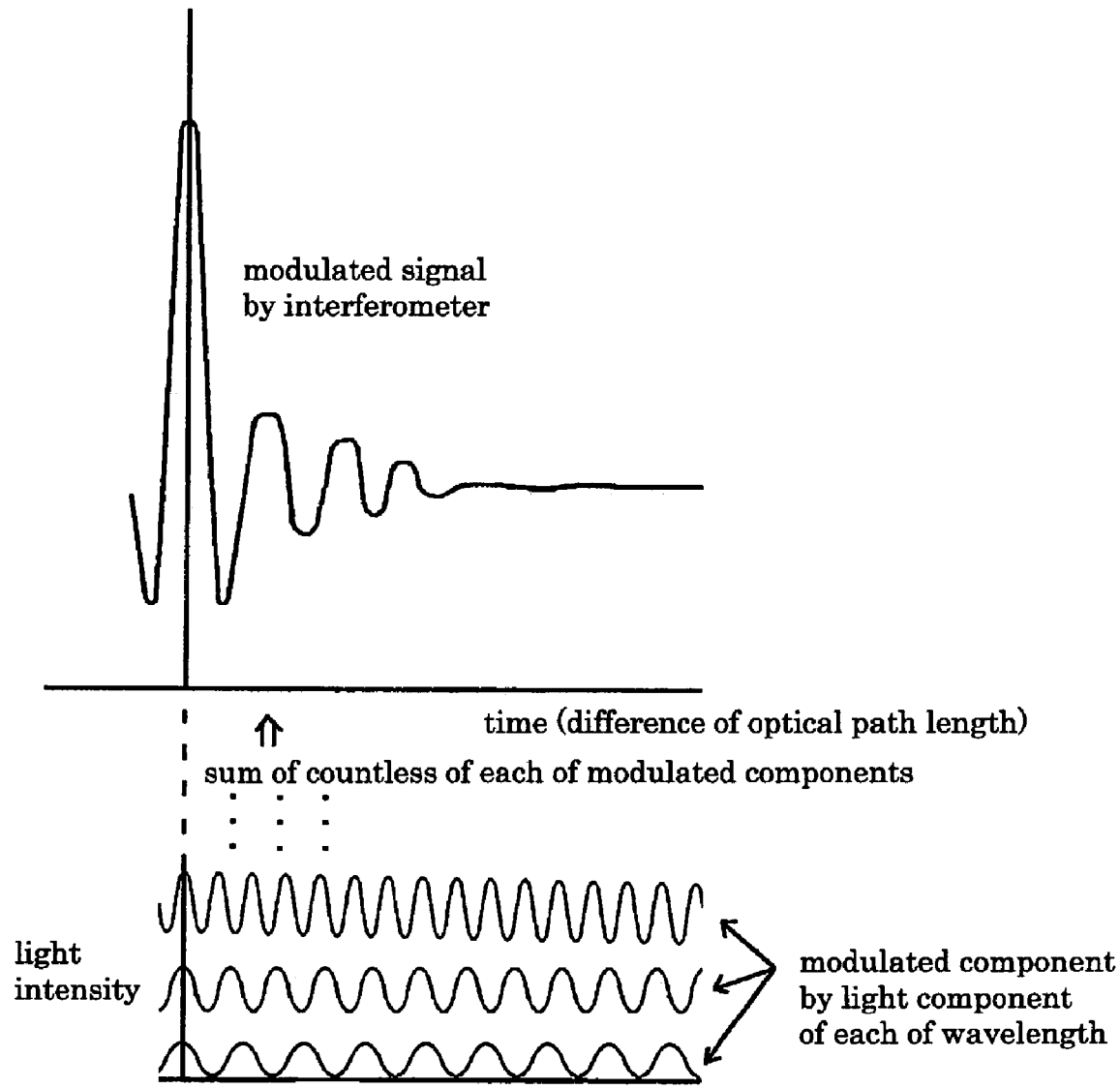
FIG. 4 is an illustrative view showing the relation between a modulated component of an infrared light beam of each wavelength by the interferometer and an interferogram.
Figure 5:
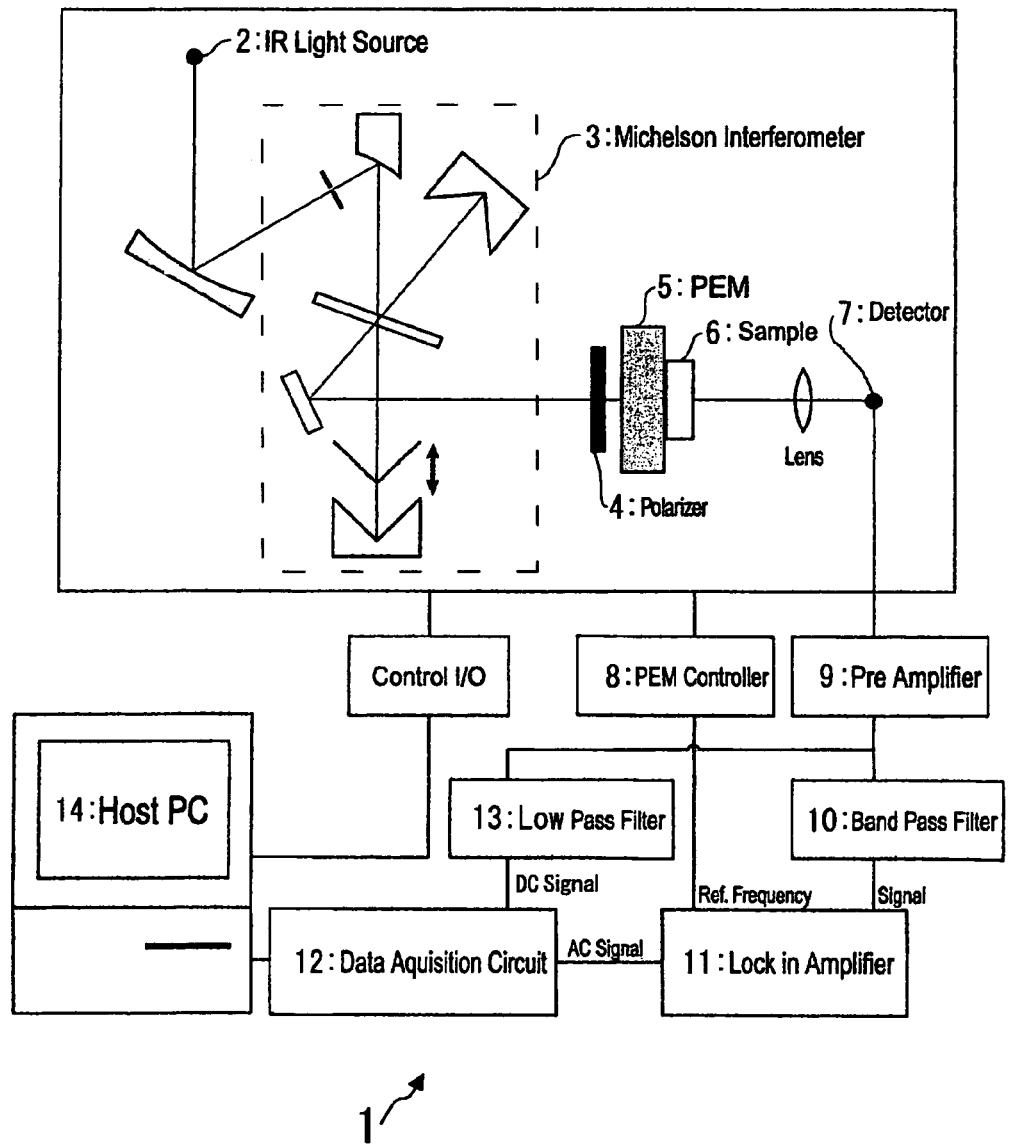
FIG. 5 is a schematic view of a conventional infrared circular dichroism measuring apparatus.
Figure 6:
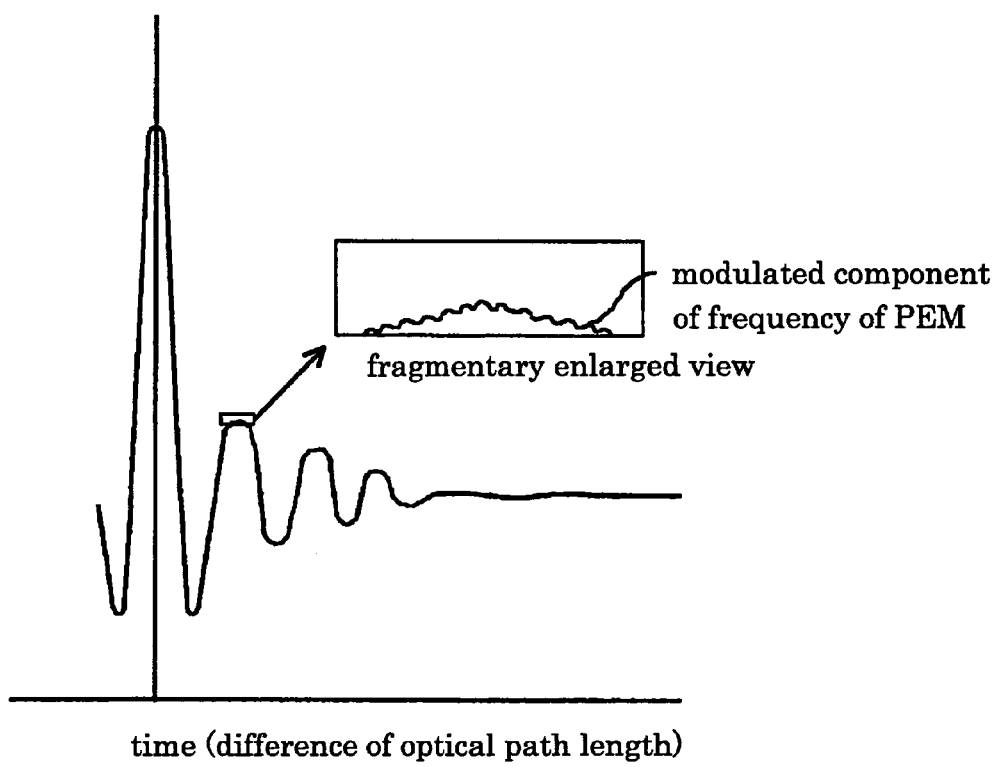
FIG. 6 is a illustrative view of a signal detected at the detector in the conventional apparatus.

As shown in FIG. 4, the light beam from the IR light source is an aggregate of countless light beams each having a wavelength and a sinusoidal-wave-like interference light beam is generated each having a different wavelength respectively for each of these light beams having a frequency.

The modulated component by the interferometer is formed as a sum of optical intensities, in which these countless sinusoidal-wave-like interference light beams are superposed. In a state where the difference of the optical path lengths in the interferometer is zero, all of the countless sinusoidal-wave-like interference light beams strengthen each other and the resultant intensity becomes maximum, however, as the moving mirror of the interferometer moves and the difference of the optical path lengths becomes longer, the countless sinusoidal-wave-like interference light beams rapidly weaken each other and, as a result, the modulated component by the interferometer is rapidly attenuated.

However, in the invention, the attenuation of the intensity can be suppressed by moderating the rapid weakening among the interference light beams by narrowing down the wavelength regions by the selective transmitter.

Therefore, the ratio of the intensity around the center burst and the intensity of edge portion of the interferogram is moderated and the modulation frequency becomes lowered resulting in a relatively smooth shape. Therefore, according to the invention, the dynamic range of the interferogram can be improved.

That is, in the conventional art, the dynamic range is limited because a sufficient intensity can not be obtained in a region where the modulated component by the interferometer is remarkably attenuated, the S/N ratio becomes degraded and the contribution by the noise component can not be ignored.

However, according to the invention, the intensity of the modulated component becomes higher compared to the conventional one even in this region since the rapid attenuation of the intensity can be suppressed and the dynamic range can be improved since the lowering of S/N ratios and quantization errors in AD conversions are suppressed.

The signal detected by the detector 107, after being amplified by a pre amplifier 109, passes through a signal processing system (AC signal extractor) comprising a band pass filter 110, a lock in amplifier 111 and a data acquisition circuit 112 and an interferogram produced from a clockwise circularly polarized light beam and a counterclockwise circularly polarized light beam is extracted.

That is, only the signal in a predetermined frequency band containing a modulation frequency of PEM 105 is passed through the band pass filter 110 and the component having a modulation frequency of PEM is lock-in-detected using a synchronized signal by the lock in amplifier 111. Then, a sampling is conducted with a predetermined time constant and an alternate current signal having intensity variation of modulation component by the interferometer 103 can be obtained.

In addition, as described above, according to the invention, the time constant of the lock in amplifier can be made longer and the S/N ratio can be improved since the modulation frequency of the modulation component by the interferometer is lowered and its shape becomes relatively smooth.

On the other hand, the signal detected by the detector 107, after being amplified by the pre amplifier 109, passes through a low pass filter 113 and a data acquisition circuit 112 (DC signal extractor) and the interferogram produced from infrared absorption is extracted.

Based on the interferograms produced from each of the clockwise and counterclockwise circularly polarized light beams and the interferograms produced from the infrared absorption extracted as above, a Fourier transformation is conducted at a computer 114 to calculate a circular dichroism spectrum that is the difference spectrum (ΔA) between absorption spectra produced from each of clockwise and counterclockwise polarized light beams.

Figure 7:
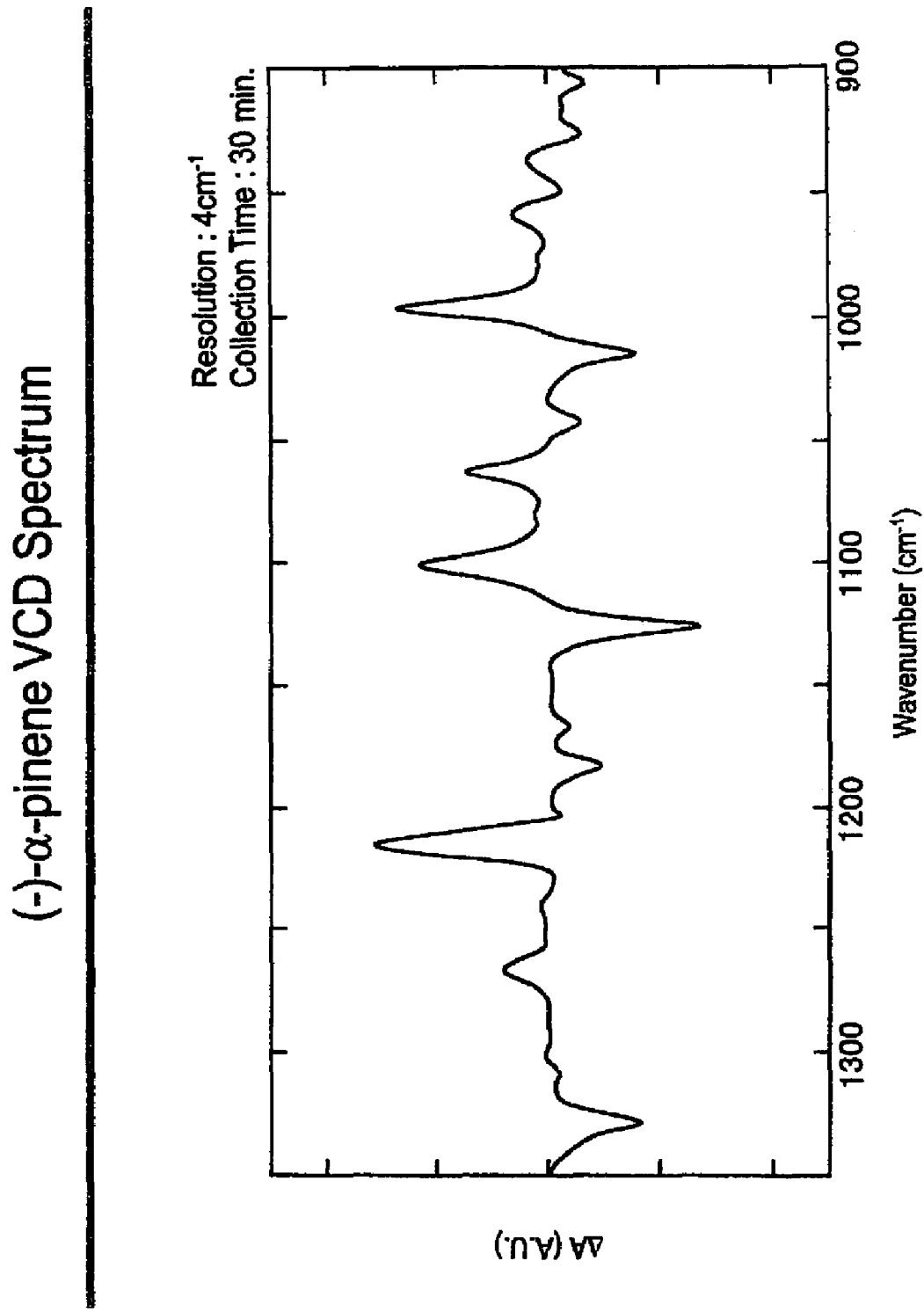
FIG. 7 shows a VCD spectrum of (−)-α-pinene measured using an infrared circular dichroism measuring apparatus according to the invention.

Using an infrared circular dichroism measuring apparatus according to the above embodiment, a VCD spectrum of (−)-α-pinene was measured. The result of the measurement is shown in FIG. 7. The measurement finished in a short time of 30 minutes and data having a sufficient accuracy for structural analysis could be obtained.

As described above, according to the infrared circular dichroism measuring apparatus and the infrared circular dichroism measuring method of the present invention, since a selective transmitter that selectively transmits only the light beam in a specific wavelength region in the infrared light from the IR light source is provided, the measuring time and measuring accuracy are improved in terms of the following items.

By selecting and using a detector that has a high sensitivity in the specific wavelength regions, high sensitivity measurements can be conducted and the integration for improving the S/N ratio can be decreased. Therefore, the time necessary for a measurement can be shortened.

By narrowing down the wavelength regions using the selective transmitter, the rapid weakening among the interference light beams can be moderated and the attenuation of the intensity can be suppressed. Therefore, the dynamic range can be improved.

When a PEM is used as the circularly polarized light generator, by setting the central wavelength of PEM with the specific wavelength region, each circularly polarized light can be efficiently generated in all the measured wavelength regions and the measurements can be conducted efficiently.

When a PC-type MCT detector is used as the detector, the wavelength regions are narrowed and the light in the regions not necessary for measurements is cut. Therefore, the incident light intensity into the detector is drastically reduced and measurements can be conducted in the intensity region where linear responses can be obtained. Then, measurements can be conducted without any influence on their accuracy.

When a lock in amplifier is used as the AC extractor, the modulation frequency of the modulated component by the interferometer is lowered and its shape becomes relatively smooth. Therefore, the time constant of the lock in amplifier can be made longer and the S/N ratio can be improved.

Furthermore, according to the infrared circular dichroism measuring apparatus and the infrared circular dichroism measuring method of the invention, by providing a selective transmitter and narrowing down the wavelength region of infrared absorption bands corresponding to the vibration modes of specific structures in a sample molecule, means for clarifying easily the relation between circular dichroism spectra of specific absorption bands and molecular structures can be obtained even in the infrared region where their assignment is very complicated.

What is claimed is:

1. An infrared circular dichroism measuring apparatus comprising:
    an IR light source radiating IR light beams;
    an interferometer for allowing the IR light beams to interfere to generate an interference light beam;
    a polarized light beam generator for making the interference light beam into a linearly polarized light beam;
    a circularly polarized light beam generator for converting the linearly polarized light beam into clockwise and counter clockwise circularly polarized light beams at a predetermined modulation frequency and irradiating the circularly polarized light beams on a sample;
    a detector for detecting the circularly polarized light beams that have passed through the sample and generating a detection signal;
    a DC signal extractor for extracting from the detected signal an interferogram by the IR absorption of the sample;
    an AC signal extractor for extracting from the detected signal an interferogram by each of the clockwise and counterclockwise circularly polarized light beams;
    a calculator for conducting a Fourier transformation and calculating the circular dichroism and IR absorption, based on each of the interferograms extracted by the extractors; and
    a selective transmitter for narrowing down the wavelength region to be measured, based on a wavelength region in an IR absorption band corresponding to a vibration mode of a structure to be measured in the sample molecule.

2. The infrared circular dichroism measuring apparatus according to claim 1, wherein the circularly polarized light beam generator is a photoelastic modulator.

3. The infrared circular dichroism measuring apparatus according to claim 2, wherein the photoelastic modulator sets its central wavelength based on a measurement wavelength region selected by the selective transmitter.

4. The infrared circular dichroism measuring apparatus according to claim 1, wherein the AC signal extractor comprises a lock in amplifier.

5. The infrared circular dichroism measuring apparatus according to claim 1, wherein a wavelength region in which the detector has a high sensitivity is defined based on a wavelength region to be measured selected by the selective transmitter.

6. The infrared circular dichroism measuring apparatus according to claim 1, wherein the selective transmitter is an optical filter for selectively irradiating on the sample a light beam of a wavelength region in an IR absorption band corresponding to a vibration mode of a specific structure in the sample molecule among IR light beams from the IR light source, and/or an electric filter for selectively transmitting a signal component of a specific region defined based on a vibration mode of a structure to be measured among interference signals by light beams at each wavelength, that are the components of a signal modulated by the interferometer.

7. The infrared circular dichroism measuring apparatus according to claim 6, wherein the relation between the structure to be measured and the wavelength region selected by the selective transmitter is expressed by at least one of the following ① to ⑦:
    ① for the structure NH, the wavelength region to be selected for measurement is 3,700–3,100 $cm^{-1}$;
    ② for the structure CH stretching vibration, the wavelength region to be selected for measurement is 3,000–2,800 $cm^{-1}$;

③ for the structure C=O, the wavelength region to be selected for measurement is 1,700 cm$^{-1}$; ④ for the structure amide I (protein), the wavelength region to be selected for measurement is 1,640 cm$^{-1}$;

⑤ for the structure amide II (protein), the wavelength region to be selected for measurement is 1,550 cm$^{-1}$;

⑥ for the structure CH bending vibration, the wavelength region to be selected for measurement is 1,500–1,300 cm$_{-1}$; and ⑦ for the structure C-O-C (sugar), the wavelength region to be selected for measurement is 1,100–900 cm$^{-1}$.

8. An infrared circular dichroism measuring method comprising the steps of:

generating an interference light beam by allowing IR light beams radiated from anIR light source to interfere by use of an interferometer;

after making the interference light beam into a linearly polarized light beam, converting the linearly polarized light beam into a clockwise and a counterclockwise circularly polarized light beams at a predetermined modulation frequency and irradiating the converted light beams on a sample;

detecting the circularly polarized light beams which have passed through the sample and generating a detection signal;

extracting from the detected signal an interfero gram by each of the clockwise and the counterclockwise circularly polarized light beams;

conducting a Fourier transformation and calculating a circular dichroism, based on the interferograms; and narrowing down the wavelength region to be measured, based on an IR absorption wavelength region corresponding to a vibration mode of the structure to be measured of a sample molecule.

9. The infrared circular dichroism measuring method according to claim 8, wherein the circularly polarized light beam is generated by a photoelastic modulator.

10. The infrared circular dichroism measuring method according to claim 9, wherein the central wavelength of the photoelastic modulator is set based on the selected wavelength region to be measured.

11. The infrared circular dichroism measuring method according to claim 8, wherein a lock in amplifier is used for the extracting.

12. The infrared circular dichroism measuring method according to claim 8, wherein a detector is used for detecting the circularly polarized light beams which have passed through the sample and generating a detection signal and wherein a wavelength region in which the detector has a high sensitivity is defined based on the selected wavelength region to be measured.

13. The infrared circular dichroism measuring method according to claim 8, wherein the wavelength region to be measured is narrowed down by selectively irradiating a light beam in an IR absorption wavelength region corresponding to the vibration mode of a specific structure in a sample molecule among the IR light beams from the IR light source, on a sample, using an optical filter, and/or by selectively transmitting a signal component of a specific region defined based on a vibration mode of the structure to be measured among interference signals by light beams at each wavelength, that are components of a signal modulated by the interferometer, using an electric filter.

* * * * *